United States Patent
Shimokita

(10) Patent No.: US 9,320,437 B2
(45) Date of Patent: Apr. 26, 2016

(54) INTRAVITAL OBSERVATION DEVICE

(75) Inventor: Ryo Shimokita, Hamamatsu (JP)

(73) Assignee: GENIAL LIGHT CO., LTD., Hamamatsu-shi (JP)

( * ) Notice: Subject to any disclaimer, the term of this patent is extended or adjusted under 35 U.S.C. 154(b) by 980 days.

(21) Appl. No.: 13/518,377

(22) PCT Filed: Dec. 22, 2010

(86) PCT No.: PCT/JP2010/073219
§ 371 (c)(1),
(2), (4) Date: Jun. 21, 2012

(87) PCT Pub. No.: WO2011/078266
PCT Pub. Date: Jun. 30, 2011

(65) Prior Publication Data
US 2012/0257034 A1 Oct. 11, 2012

(30) Foreign Application Priority Data

Dec. 22, 2009 (JP) .................................. 2009-290058
Apr. 26, 2010 (JP) .................................. 2010-100497

(51) Int. Cl.
*H04N 7/18* (2006.01)
*A61B 5/00* (2006.01)
*A61B 5/026* (2006.01)

(52) U.S. Cl.
CPC ............. *A61B 5/0059* (2013.01); *A61B 5/0077* (2013.01); *A61B 5/489* (2013.01); *A61B 5/0261* (2013.01); *A61B 5/6826* (2013.01); *A61B 2562/185* (2013.01)

(58) Field of Classification Search
USPC .......................................................... 348/77
See application file for complete search history.

(56) References Cited

U.S. PATENT DOCUMENTS

2010/0177182 A1 7/2010 Kagenow et al.

FOREIGN PATENT DOCUMENTS

| JP | 08033627 A | 2/1996 |
|----|------------|--------|
| JP | 2000300568 | 10/2000 |
| JP | 2000300568 A | * 10/2000 |
| JP | 2002092616 | 3/2002 |
| JP | 2006230657 A | 9/2006 |
| JP | 2008086724 | 4/2008 |

(Continued)

OTHER PUBLICATIONS

ISA Japan, International Search Report of PCT/JP2010/073219, Mar. 1, 2011, WIPO, 1 page.
"General Rules of Photodiodes for Fiber Optic Transmission," Reference No. JIS C 5990: 1997, Japanese Standards Association, 1997, 3 pages. (See p. 1, explanation of relevance).

(Continued)

*Primary Examiner* — Andy Rao
*Assistant Examiner* — Tyler Edwards
(74) *Attorney, Agent, or Firm* — Alleman Hall McCoy Russell & Tuttle LLP

(57) ABSTRACT

Disclosed is an intravital observation device that has a simple structure and that can observe a foreign material and both blood vessels of an artery and a vein inside a living body without requiring an angiographic agent, X-rays, or harming the body. The intravital observation device comprises a light source that irradiates light having a wavelength peak in a wavelength region of 800 to 1000 nm onto the living body and an imaging device that outputs an image data obtained by receiving the light that has passed through the living body. The imaging device is a digital camera whose minimum detection light amount per output at a time when receiving the light of 0.4 to 10 μW is less than or equal to 0.055 μW/bit.

6 Claims, 14 Drawing Sheets

(56) References Cited

FOREIGN PATENT DOCUMENTS

| | | | |
|---|---|---|---|
| JP | 2008086724 A | * | 4/2008 |
| JP | 2008145307 | | 6/2008 |
| JP | 2009532140 A | | 9/2009 |
| JP | 2009226072 | | 10/2009 |
| JP | 2009238205 | | 10/2009 |

OTHER PUBLICATIONS

"The CCD Image Sensor", CHRONIX Ltd., retrieved form JPO database Feb. 12, 2015, publication date unknown, 4 pages. (See p. 2, translation of relevant portion).

Japanese Patent Office, Decision of Refusal Issued in Japanese Patent Application No. 2011-547612, Aug. 4, 2015, 3 pages.

* cited by examiner

INTRAVITAL OBSERVATION DEVICE

FIELD OF THE ART

This invention relates to an intravital observation device that can easily obtain a living body perspective image in real time on an arbitrary place.

BACKGROUND ART

For example, an accident of amputating a finger, a hand, an arm, a foot or a leg might happen such that the finger or the limb is wedged by a door or a machine at home or in a factory or the like. In a case where the finger or the limb is amputated due to the accident, tissue such as a blood vessel at the cut portion is in a crushed state, unlike in a case where the finger or the limb is cut by a keen edged knife or the like. As a result of this, conventionally, in order to replant the amputated portions, the blood vessels are joined and blood circulation confirmed by the use of a Doppler or a laser Doppler blood flow meter. However, this approach requires one highly skilled in technology and with sufficient experience to join the blood vessels and confirm blood circulation by the use of the blood flow meter.

In addition, in order to confirm whether or not the blood vessels are appropriately joined, for example, in a case where the amputated portion is the finger, the patient who is already suffering from the pain of the amputated portion is compelled to suffer further pain because a distal end of the finger is pricked so as to confirm whether or not the blood circulation is secured.

One known device to confirm the blood circulation in the blood vessel is a device for an image processing on a reflected light from the living body, to verify the position of the vein and to aid intravenous injection. However, since an image of the artery cannot be reflected by this device, it is not possible to fully make the most use of this device in case of suturing the amputated finger or limb. In addition, it is necessary for this device to conduct image processing in a manner that eliminates an influence from external light.

Furthermore, there is also a case where foreign material enters the inside of the living body as a result of an accident at home or in a factory. In this case, in order to extract the foreign material, the position of the foreign material has to be confirmed first. The position of the foreign material can be verified by the use of X-rays, however, it is difficult to conduct a surgery of extracting the foreign material with confirming the position of the foreign material in real time while irradiating the X-rays that are harmful to humans. Similarly, in a case of observing the inside of the living body through the use of an X-ray CT or an MRI, since the X-ray CT or the MRI is large-scale and the X-rays have to be used or a powerful magnetic field has to be applied, it is not possible to bring these devices in a surgery room and to conduct the surgery while observing the inside of the living body in real time.

Furthermore, in order to insert a catheter into a blood vessel, conventionally an angiographic agent is infused into the blood vessel so as to confirm the position of the blood vessel and then the catheter is inserted into the blood vessel by a doctor, depending on his or her memory concerning the position of the blood vessel. However, it also requires an advanced technique and experience to conduct an insertion of a catheter.

In addition, if affected by diabetes, one of the three major lifestyle-related diseases, the patient is superimposed on arteriosclerosis and the blood vessel is narrowed and resulting in the hematogenous disorder. In the worst case, the patient might have no other choice but to cut his or her lower limb. As a result of this, it is important to monitor the blood circulation with time.

As a technique for supporting a surgery, the Patent Document 1 discloses a technique wherein an exciting light having a specific wavelength region and a visible light are irradiated alternately on a subject to which the angiographic agent is applied, a fluorescent image to which the exciting light is irradiated and an ordinary image are obtained alternately by means of the imaging device, the obtained fluorescent image is threshold-processed by a predetermined threshold and the blood vessel image is extracted, and a composite image that is made by superimposing the extracted blood vessel image on the obtained ordinary image.

However, this technique requires the angiographic agent be injected into the subject and also requires complicated image processing.

PRIOR ART DOCUMENT

Patent Document

Patent Document 1: Japanese Unexamined Patent Application Publication No. 2009-226072

DISCLOSURE OF THE INVENTION

Problems to be Solved by the Invention

With the view to the above-mentioned present conditions, the present claimed invention intends to provide an intravital observation device that has a simple structure and that can observe a foreign material and both blood vessels of an artery and a vein inside a living body without requiring an angiographic agent, X-rays, or harming the body.

Means to Solve the Problems

Unlike X-rays, it is considered difficult for visible light to pass through the living body, however, it is known that the near-infrared light is high in transmission degree in the living body. The light in this wavelength region passes through the living tissue such as muscle, fat or bone of a human body, meanwhile, the light in this wavelength region has the characteristics of being absorbed by pigment such as hemoglobin or melanin. The present claimed invention is completed by making use of the properties of near-infrared light.

More specifically, the intravital observation device in accordance with this invention comprises a light source that irradiates light having a wavelength peak in a wavelength region of 800 to 1000 nm on a living body, and an imaging device that outputs an image data obtained by receiving the light having passed through the living body, and is characterized in that the imaging device is a digital camera whose minimum detection light amount per output at a time when receiving light of 0.4 to 10 μW is less than or equal to 0.055 μW/bit.

Since the near-infrared light of 800 to 1000 nm passes through the living tissue, an image taken by an imaging device such as a CCD camera or the like is expressed in white because the image receives the transmitted light, and the image of the blood vessel is expressed in black because the near-infrared light is absorbed by hemoglobin in blood. The technique of taking an image of a vein by making use of the characteristics of the near-infrared light is known conventionally, however, the technique of taking an image of an artery by making use of the near-infrared light is not known. More specifically, for example, if the near-infrared light is irradiated on a back surface of a finger, the light passes to a pad side of the finger while scattering inside the finger, and an image of the bone or the artery locating in the deep part of the finger disappears and only an image of the vein locating under the skin is taken.

On the contrary, the inventor of this invention has found that, opposite to expectation, it becomes possible to take the image of not only the vein but also the artery by using an imaging device having a specific sensitivity wherein the minimum detection light amount per output at a time when receiving the light of 0.4 to 10 μW is less than or equal to 0.055 μW/bit and has completed the present claimed invention.

If the intravital observation device in accordance with this invention is used, it is possible for anyone to observe the foreign material or the blood vessel inside the living body easily without requiring a special technique or experience. In addition, in accordance with this invention, it is possible to take the image of not only the vein but also the artery.

Furthermore, in accordance with this invention, since the inside of the living body can be observed without using the X-rays, even though the light is irradiated onto the living body for a long period of time, it is harmless for the human body, and since the light is just irradiated, a person being tested will never suffer pain when blood circulation is checked.

Since the intravital observation device is simple in arrangement, the intravital observation device can be downsized easily so that it is possible to bring the intravital observation device into a surgery room, to conduct joint surgery of a finger or an extremity, extraction of a foreign material or insertion of a catheter while observing the inside of the living body in real time.

The light source may not be especially limited as long as the light source irradiates the light having the wavelength peak in the wavelength region of 800 to 1000 nm, however, for example, LEDs or a laser is used, preferably. In accordance with this arrangement, since the light having a narrow wavelength region can be obtained, it is possible to obtain a clear image having less noise.

The intravital observation device in accordance with this invention is preferably provided with a cut filter that is arranged between the living body and the imaging device and that removes the light in a wavelength region of at least less than 800 nm. With an arrangement comprising the cut filter, since it is possible to block an external light (a visible light), it is possible to obtain a sharp image whose noise is reduced.

Furthermore, it is preferable that the intravital observation device in accordance with this invention comprises a diffusion plate that is arranged between the light source and the living body and that can diffuse the incident light at an angle more than or equal to 55 degrees. In accordance with this arrangement, if a plurality of LEDs are used as the light source, since the light irradiated from the multiple LEDs is diffused by the diffusion plate, it is possible to irradiate the light whose brightness is made uniform and whose irradiation unevenness is resolved onto the living body, which is the object to be observed.

In addition, it is preferable that the intravital observation device in accordance with this invention comprises a polarizing plate that is arranged between the diffusion plate and the living body. Since it is possible to irradiate the polarized light having the optimum vibration direction (the transmission axis) onto the living body because the polarizing plate is arranged in an overlapped state on the diffusion plate, it is possible to reduce reflection of the light on the surface of the living body.

In a case where the inside of the living body is observed by the use of the intravital observation device in accordance with this invention, as intended usages considered are, for example, a whole examination that examines the whole of the living body and a local examination that examines a local area of the living body.

However, in a case where the device having the same configuration is used for both the whole examination and the local examination, the specification of the device has to be tailored to the whole examination. Then in case of the local examination, the light amount passing through other than the local area becomes too much so that the transmitted light resulting from the desired local area cannot be detected accurately. As a result of this, there is a problem that the local examination becomes inaccurate.

Then, it is preferable that the intravital observation device in accordance with this invention comprises a surface luminous part that has a luminous surface facing a living body placing region and that irradiates the light onto the living body locating in the living body placing region, and a light shielding member that is mounted on the surface luminous part in a detachable manner and that blocks a part of the light emitted from the surface luminous part, wherein the imaging device is arranged on a side opposite to the surface luminous part across the living body placing region.

In accordance with the intravital observation device, since the light shielding member that blocks a part of the light emitted from the luminous surface is arranged, a range of light irradiation in the living body placing region can be narrowed so that it is possible to irradiate the light on the local area of the living body. In addition, since the light can be irradiated on the local area of the living body, it is possible to preferably obtain the living body perspective image of the local area of the living body. Furthermore, since the light shielding member is dismountable from the surface luminous part, it is possible to easily switch from obtaining the living body perspective image of whole of the living body such as, for example, a whole of a hand to obtaining the living perspective image of a local area of the living body such as a finger just by mounting or dismounting the light shielding member. In addition, it is possible for anyone to observe the foreign material or the blood vessel inside the living body easily without requiring a special technique or experience. Since the inside of the living body can be observed without using X-rays, even though the light is irradiated onto the living body for a long period of time, it is harmless for the human body, and since the light is just irradiated, a person being tested will never suffer pain when blood circulation is checked. In addition, since the intravital observation device can be downsized easily, it is possible to bring the intravital observation device into a surgery room and to conduct various surgeries while observing the inside of the living body in real time.

In order to make the imaging part receive the light that is not blocked by the light shielding member, it is preferable that the light shielding member comprises a light shielding part that blocks the light from the luminous surface and an opening part that transmits the light from the luminous surface to the living body placing region side, and the light shielding member is mounted on the surface luminous part in a detachable manner so that an opening center of the opening part located on or near an optical axis of the imaging part.

In a case where the light shielding member is arranged in a manner detachable from the surface luminous part, it is preferable to comprise a fixing mechanism that positions and fixes the light shielding member to the surface luminous part. With this arrangement, since the light shielding member is positioned when the light shielding member is fixed to the surface luminous part, the light shielding member is also positioned relative to the imaging device. As a result of this, there is no need to position the imaging part and the light shielding member each time for each examination.

In case of obtaining the living body perspective image at the local area of the living body, in order to prevent the imaging position from varying for each examination, it is preferable to comprise a positioning member that is arranged on the light shielding member and that positions the living body relative to the light shielding member so that the light that is not blocked by the light shielding member is irradiated on a predetermined portion of the living body.

As a concrete configuration of the surface luminous part, it is preferable that the surface luminous part comprises a plurality of LEDs, a case that houses the LEDs and a light transmissive member that is arranged on a light irradiation side of the LEDs in the case and that forms the luminous surface.

In addition, in a case where the inside of the living body is observed by the use of the intravital observation device in accordance with this invention, as a usage it can be conceived that the image of the living body is taken periodically in order to examine, for example, a change of the living body over time.

However, in a case where the living body is examined at periodic intervals, there is a problem that a judgment is falsely made in a comparison examination if an imaging position of the living body perspective image at one time differs from an imaging position of the living body perspective image taken at another time.

Then, it is preferable that the intravital observation device in accordance with this invention comprises a surface luminous part that has a luminous surface facing a living body placing region and that irradiates the light onto the living body locating in the living body placing region, and a positioning part that positions the living body relative to the luminous surface of the surface luminous part, wherein the imaging device is positioned relative to the luminous surface of the surface luminous part.

In accordance with this arrangement, since the living body is positioned relative to the luminous surface by the positioning member, it is possible to irradiate the light on a predetermined area of the living body. Furthermore, since the image of the living body is taken by the imaging part that is positioned relative to the surface luminous part, it is possible to simplify the process after the image is taken, such as by comparing the images obtained by the imaging part. In addition, it is possible for anyone to observe the foreign material or the blood vessels inside the living body easily without requiring special techniques or experience. Furthermore, since the inside of the living body can be observed without using X-rays, even though the light is irradiated onto the living body for a long period of time, it is harmless for the human body, and since the light is just irradiated, a person being tested will never suffer pain when blood circulation is checked. In addition, since the intravital observation device can be downsized easily, it is possible to bring the intravital observation device into a surgery room and to conduct various surgeries while observing the inside of the living body in real time.

In order to make the effect of this invention more remarkable, it is preferable that the intravital observation device observes a hand or a foot, and the positioning member positions the hand or the foot by making contact with a predetermined finger or toe of the hand or the foot.

In order to determine a position of the predetermined area of the living body in an image taken by the imaging part, it is preferable that the positioning member positions the living body in a plane direction of the luminous surface. The living body may be positioned in a direction orthogonal to the plane direction relative to the surface luminous part.

In order to make it possible to preferably obtain the living body perspective image of the local area of the living body by irradiating the light only on the local area of the living body, it is preferable to further comprise a light shielding member that is arranged between the living body placing region and the luminous surface of the surface luminous part and that blocks a part of the light emitted from the luminous surface. At this time, in order to make it possible to securely irradiate the light that is not blocked by the light shielding member on the predetermined area of the living body, it is preferable that the positioning member is arranged on the light shielding member and positions the living body relative to the light shielding member so that the light that is not blocked by the light shielding member is irradiated on the predetermined portion of the living body.

As a concrete arrangement of the surface luminous part, it is preferable that the surface luminous part comprises a plurality of LEDs, a case that houses the LEDs and a light transmissive member that is arranged on a light irradiation side of the LEDs in the case and that forms the luminous surface.

Effect of the Invention

In accordance with the present claimed invention, it is possible for anyone to observe a foreign material or a blood vessel in a living body easily without requiring special techniques or experience. Furthermore, in accordance with this invention, it is possible to take an image of not only a vein but also an artery.

In addition, in accordance with this embodiment, even though the light is irradiated onto the living body for a long period of time, it is harmless for the human body, and since the light is just irradiated, a person being tested will never suffer pain.

Furthermore, since the intravital observation device can be downsized easily, it is possible to bring the intravital observation device into a surgery room and to conduct various kinds of surgery while observing the inside of the living body in real time.

BEST MODES OF EMBODYING THE INVENTION

<First Embodiment>

A first embodiment of this invention will be explained with reference to drawings.

Figure 1:
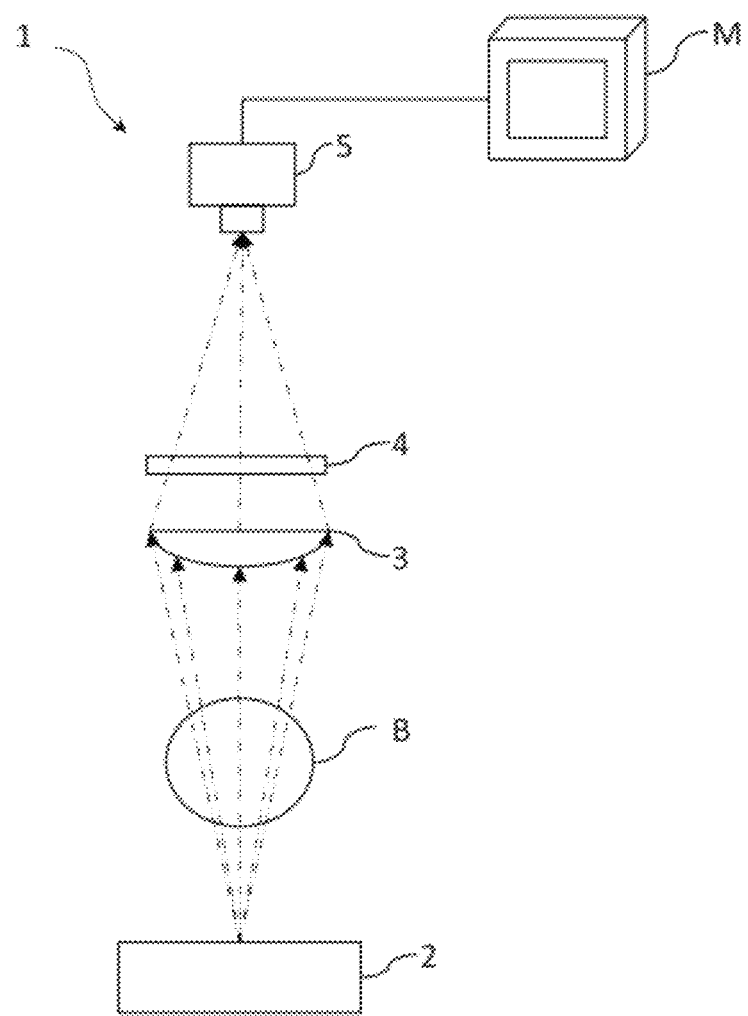
FIG. 1 is a configuration diagram of an intravital observation device in accordance with a first embodiment of this invention.

An intravital observation device 1 in accordance with the first embodiment comprises, as shown in FIG. 1, a light source 2, a light condensing lens 3, a cut filter 4 and an imaging device 5.

Each part will now be described in detail.

The light source 2 irradiates a living body (B) with near-infrared light having a wavelength peak in a region of 800 to 1000 nm, and LEDs or a laser can be used as the light source 2. For example, in a case where a hand of a grown-up is an object to be observed by the use of the LEDs of 170 mW having the wavelength peak in the region of 810 nm as the light source 2, about 28 pieces of the LEDs may be used by being laid on a surface of a planate substrate. Meanwhile, in a case where the laser is used as the light source 2, a Nd:YAG laser or a semiconductor laser may be used.

The light condensing lens 3 condenses the light that has passed through the living body (B), and for example, a plane-convex lens may be used as the light condensing lens 3.

It is preferable that a monitor stage (not shown in drawings) whose carrying surface has translucency is arranged between the light source 2 and the light condensing lens 3 to carry the living body (B) as being the object to be observed. If the monitor stage is arranged, in a case where, for example, a finger is cut, it is possible to conduct a joint surgery of the finger with monitoring a blood vessel in a cut portion of the finger by placing the hand on the monitor stage. In addition, the light source 2 and the monitor stage may be separately arranged or integrated.

The cut filter 4 cuts at least the light in the wavelength region less than 800 nm, and a filter having desired characteristics may be appropriately selected as the cut filter 4 among filters available in the market. Since the cut filter 4 is arranged, it is possible to block an external light (visible light) so that noise can be reduced, thereby being enabled to obtain a sharper image.

The imaging device 5 is a digital camera that outputs image data obtained by receiving the light that has passed through the cut filter 4, and has a specific sensitivity wherein a minimum detection light level per unit output is less than or equal to 0.055 μW/bit when receiving the light of 0.4~10 μW. For example, a CCD camera or a CMOS camera or the like may be used as the imaging device 5. It is necessary to connect the imaging device 5 with an arbitrary display device (M) in order to check an image obtained by the imaging device 5, however, the display device (M) may be previously arranged for the intravital observation device 1, or an externally arranged display device (M) may be used.

Figure 2:
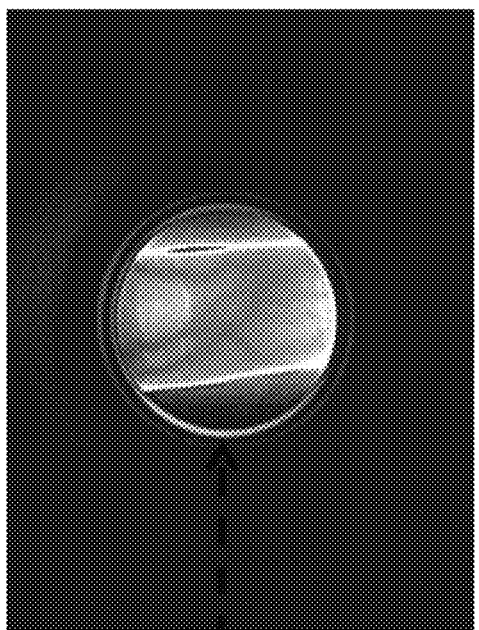
FIG. 2 is a photograph of a finger taken by the use of the intravital observation device in accordance with this embodiment.
Figure 2:
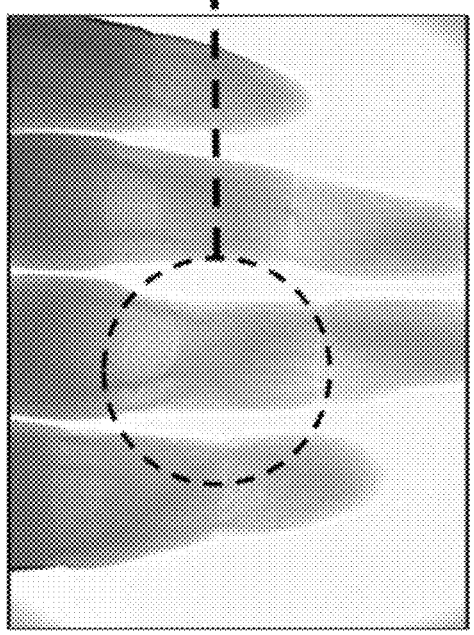
Figure 2:
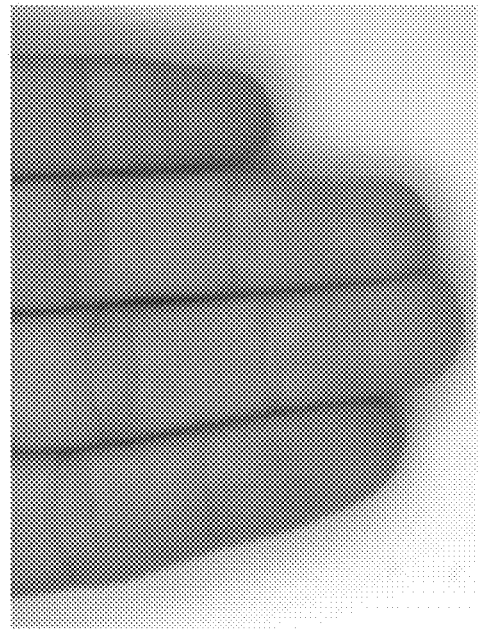

FIG. 2(a) shows an image wherein a blood vessel of a finger is observed by the use of the intravital observation device 1 whose imaging device 5 is a CCD camera having the minimum detection light level per unit output of less than or equal to 0.055 μW/bit when the light of 0.4~10 μW is received with placing the finger on the monitor stage whose carrying surface has the translucency and irradiating the near-infrared light from a back surface of the finger. As shown in FIG. 2, it is verified that the blood vessel expressed in black is clearly observed. The CCD camera has sensitivity wherein a detection light intensity is 0.33 μW when a digital output (hereinafter just called as a luminance output) that corresponds to luminance is 11 bit and the detection light intensity is 10.21 μW when the luminance output is 197 bit, and a linear relation is recognized between the luminance output and the detection light intensity in the range of 0.33~10.21 μW of the detection light intensity. Meanwhile, in a case where the CCD camera whose sensitivity is lower (the minimum detection light intensity is more than 0.055 μW/bit) than the above CCD camera, it was not possible to observe the blood vessel of the finger as shown in FIG. 2(b). FIG. 2(c) is an image wherein the blood vessel of the finger is observed in a state that a light shielding member 8, to be described later, is mounted.

In accordance with the intravital observation device 1 of this embodiment, it is possible for anyone to observe a foreign material or a blood vessel in a living body easily without requiring special techniques or experience. In addition, since the intravital observation device 1 is provided with the imaging device 5 having the specific sensitivity wherein the minimum detection light level per unit output is less than or equal to 0.055 μW/bit when receiving the light of 0.4~10 μW, it is possible to take an image of not only a vein but also an artery.

Furthermore, in accordance with this embodiment, since the inside of the living body can be observed without using X-rays, even though the light is irradiated onto the living body for a long period of time, it is harmless for the human body, and since the light is just irradiated, a person being tested will never suffer pain when blood circulation is checked.

In addition, since an arrangement of the intravital observation device 1 is simple, the intravital observation device 1 can be downsized easily so that it is possible to bring the intravital observation device 1 into a surgery room and to conduct a joint surgery of a finger or an extremity, extraction of a foreign material or insertion of a catheter while observing the inside of the living body in real time.

<Second Embodiment>

A second embodiment of this invention will be explained with reference to the drawings. An explanation will be made with a focus on a point that is different from that of the first embodiment.

Figure 3:
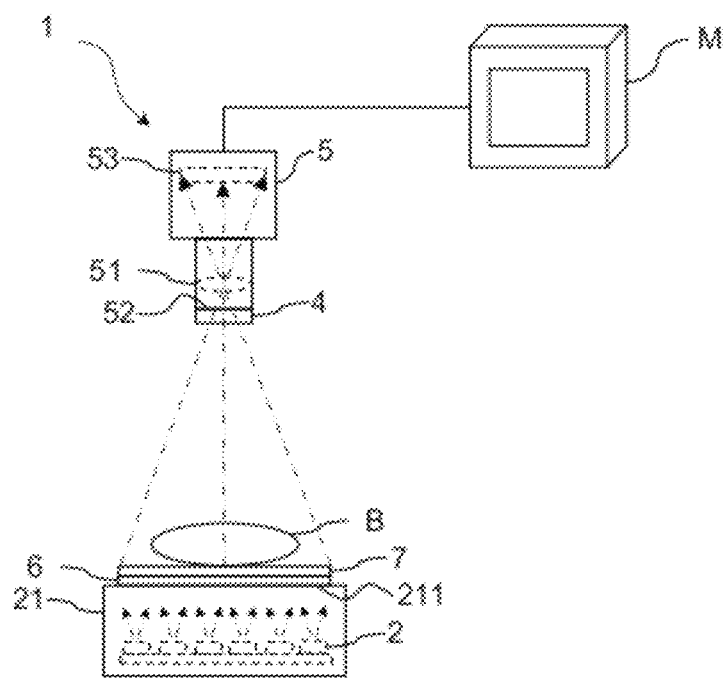
FIG. 3 is a configuration diagram of an intravital observation device in accordance with a second embodiment of this invention.

The intravital observation device 1 in accordance with the second embodiment comprises, as shown in FIG. 3, the light source 2, a diffusion plate 6, a polarizing plate 7, the cut filter 4 and the imaging device 5. In this embodiment, a plurality of LEDs laid on a surface of a planate substrate are used as the light source 2 and housed in a case 21 where an irradiation port 211 is formed.

The diffusion plate 6 diffuses the light irradiated from the multiple LEDs so as to uniformize the luminance of the light irradiated from the irradiation port 211 of the case 21 and irradiates the light of even irradiation onto the living body (B). The diffusion plate 6 is arranged to cover the irradiation port 211. Various kinds of a plate to which a light diffusion characteristics is given by making use of light scattering such as a light transmission substrate whose surface is provided with concavity and convexity with an embossed process or a surface texturing so as to make its surface in a frosted glass state, a light transmission substrate on a surface of which a white paint is applied with gaps provided and a light transmission substrate inside of which particles that causes light scattering are contained can be used as the diffusion plate 6. Among these diffusion plates 6, a substrate that is made of, for example, acetal resin and that can diffuse incident light at 55 degrees and over is preferably used. If the diffusion plate having the diffusing angle of 55 degrees and over is used, irradiation unevenness can be resolved so that it is possible to irradiate the light on the object to be tested uniformly.

In order to verify this, the LEDs are mounted on a light shielding plate having bores whose diameter is 5 mm and a thickness of the diffusion plate to be placed on the light shielding plate is varied, and a ratio (Im/I) between a light intensity (I) just above the LED and a light intensity (Im) just above a center point between two LEDs when two LED are arranged at 10 mm intervals is obtained. The nearer to 1 the value of Im/I is, the more the illumination unevenness is resolved. The obtained result is shown in table 1.

TABLE 1

| item | current (mA) | half width (dot) | divergence angle of light source (°) | divergence angle of diffusion plate (°) | Im/I |
|---|---|---|---|---|---|
| without | 4 | 13 | 19.9 | — | — |
| diffusion plate | 5 | 13 | 19.9 | — | — |
| | 6 | 14 | 21.3 | — | — |
| | 7 | 14 | 21.3 | — | — |
| | 8 | 14 | 21.3 | — | — |
| | 9 | 14 | 21.3 | — | — |
| diffusion plate | 4 | 87 | 19.9 | 58.9 | 0.85 |
| made of acetal | 5 | 94 | 19.9 | 60.8 | 0.86 |
| resin | 6 | 93 | 21.3 | 60.0 | 0.86 |
| (t = 5 mm) | 7 | 109 | 21.3 | 63.7 | 0.88 |
| | 8 | 115 | 21.3 | 64.8 | 0.89 |
| | 9 | 119 | 21.3 | 65.5 | 0.89 |
| diffusion plate | 4 | 27 | 19.9 | 16.4 | 0.52 |
| made of acetal | 5 | 63 | 19.9 | 44.1 | 0.79 |
| resin | 6 | 93 | 21.3 | 55.0 | 0.86 |
| (t = 10 mm) | 7 | 108 | 21.3 | 58.9 | 0.88 |
| | 8 | 109 | 21.3 | 59.1 | 0.88 |
| | 9 | 124 | 21.3 | 62.2 | 0.90 |

As a result of this, in a case where the diffusion plate that can diffuse the light emitted from the light source at an angle of 55 degrees or over, every value of Im/I becomes 0.85 or over so that it is verified that a sufficient effect of resolving the illumination unevenness is obtained.

The polarizing plate 7 is arranged in piles on a surface, located at the opposite side of the light source of the diffusion plate 6 and creates a linearly-polarized light from the uniformized light diffused by the diffusion plate 6. The polarizing plate 7 used is a film shaped plate made of, for example, resin. Since the polarized light whose vibration direction (transmission axis) is optimum can be irradiated onto the living body (B) because the polarizing plate 7 is arranged in piles on the diffusion plate 6, it is possible to reduce reflection of the light on the surface of the living body (B). In this embodiment, it is possible to observe the living body (B) by placing the living body (B) on the polarizing plate 7.

In this embodiment, it is possible to obtain an image whose contrast is clear by adjusting the light quality and the light intensity of the light irradiated onto the living body (B) as being the object to be observed.

In this embodiment, the cut filter 4 is arranged on a light introducing inlet 52 of the imaging device 5 so that it is possible to prevent external light, such as sunlight, from entering the imaging device 5.

Unlike as in the first embodiment, the intravital observation device 1 in accordance with the second embodiment is not provided with the condensing lens 3; however, a condensing lens 51 is built in the imaging device 5. The light that has passed through the living body (B) is condensed by the condensing lens 51 and an image is provided on an acceptance surface of an imaging element 53 such as a CCD image sensor or the like. It is possible to make the whole region of an irradiation inlet 211 of the case 21 of the light source 2 as an imaging range by selecting an appropriate light condensing lens 51. For example, in a case where a size of the irradiation inlet 211 is 80×100 mm, the light condensing lens 51 whose focal length is 6 to 10 mm is preferably used.

<Third Embodiment>

A third embodiment of this invention will be explained with reference to the drawings. Codes in FIG. 4 to FIG. 12 concerning the third embodiment do not necessarily coincide with the codes in FIG. 1 to FIG. 3 concerning the first embodiment and the second embodiment, and the codes in FIG. 4 to FIG. 12 are designated independently.

The intravital observation device 100 in accordance with this embodiment irradiates the light on a living body such as a hand or a foot, takes an image of the transmitting light that has passed through the living body and obtains a living body perspective image that indicates a blood vessel or a foreign material in the living body.

Figure 4:
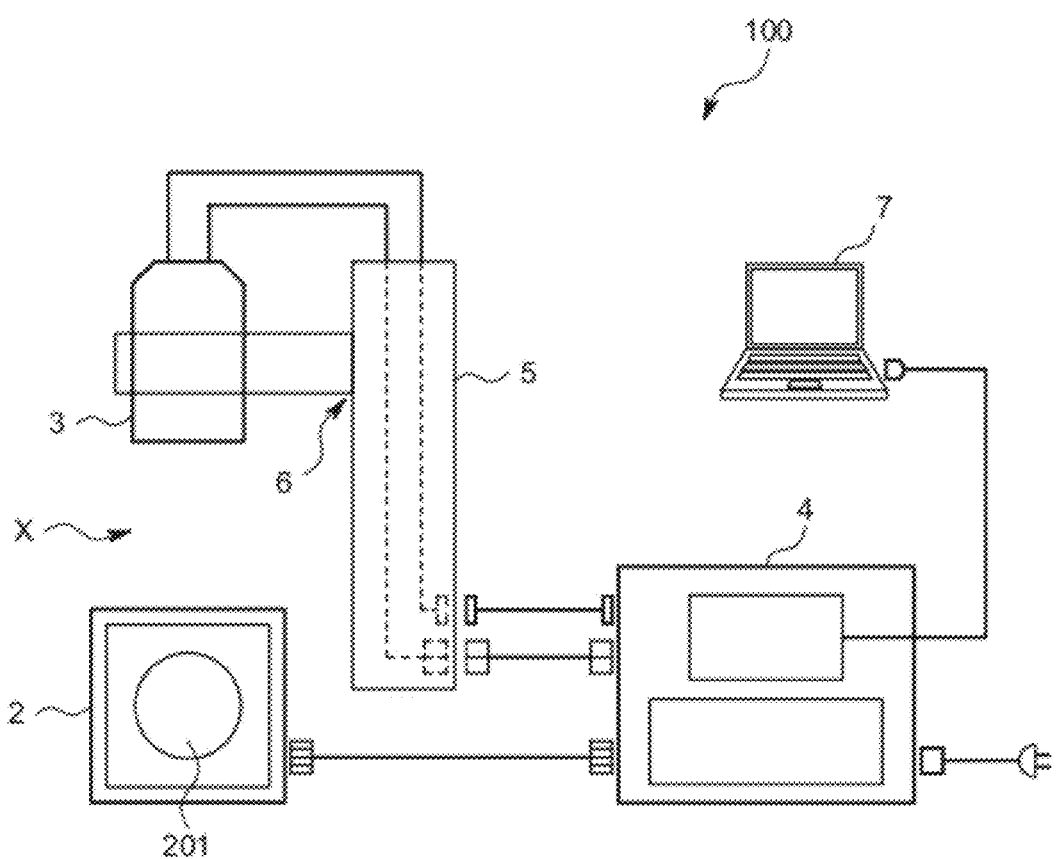
FIG. 4 is a pattern diagram showing a configuration of an intravital observation device in accordance with a third embodiment of this invention.
Figure 5:
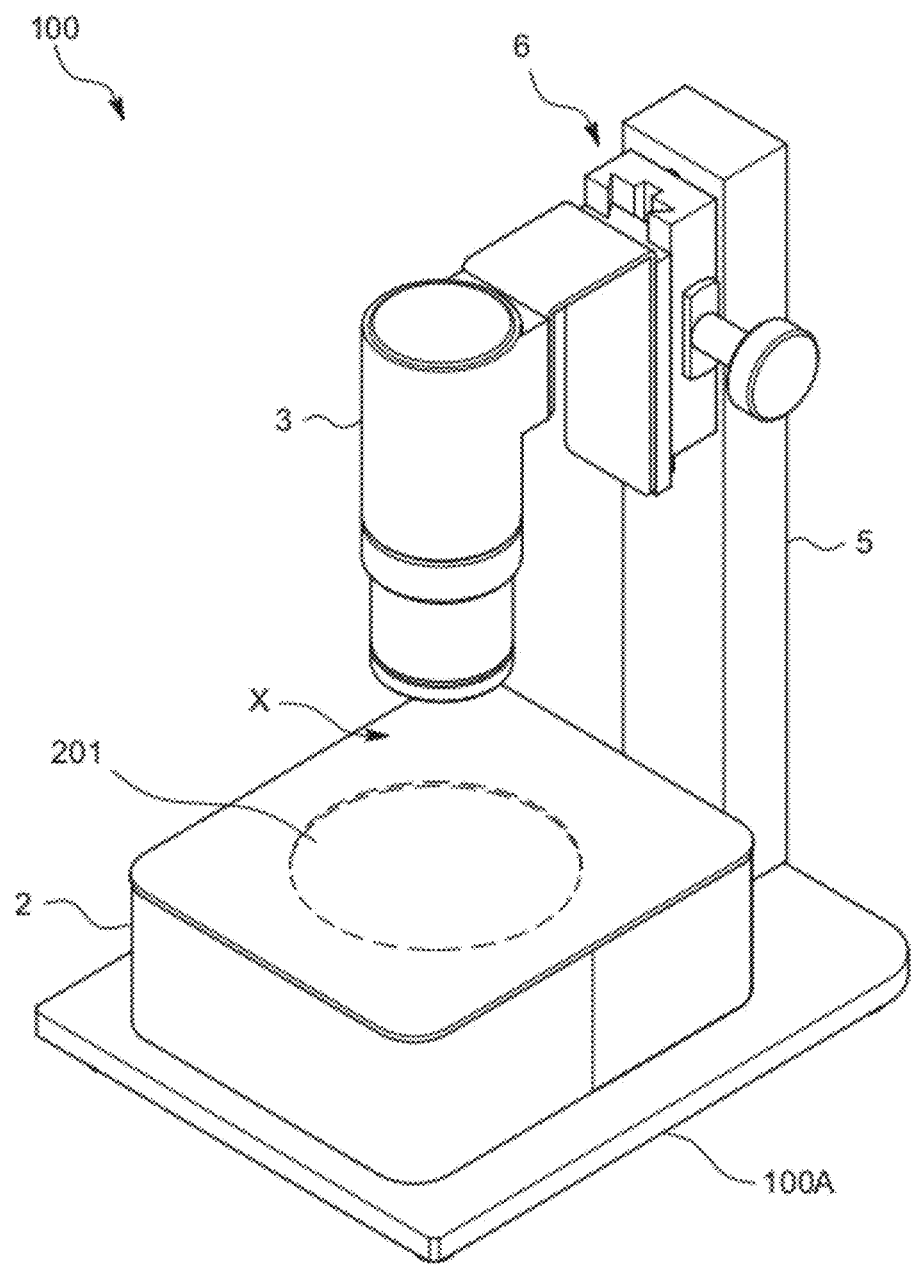
FIG. 5 is a perspective view showing a configuration of the intravital observation device (with no light shielding member mounted) of this embodiment.

Concretely, the intravital observation device 100 comprises, as shown in FIG. 4 and FIG. 5, a surface luminous part 2 that has a luminous surface 201 facing a living body placing region (X) and that irradiates the light onto the living body in the living body placing region (X), and an imaging part 3 that is arranged in a side opposite of the surface luminous part 2 of the living body placing region (X) and that receives the light having passed through the living body in the living body placing region (X) and outputs the image data. In this embodiment, the surface luminous part 2 is arranged on the downside across the living body placing region (X) and the imaging part 3 is arranged on the upper side.

Figure 6:
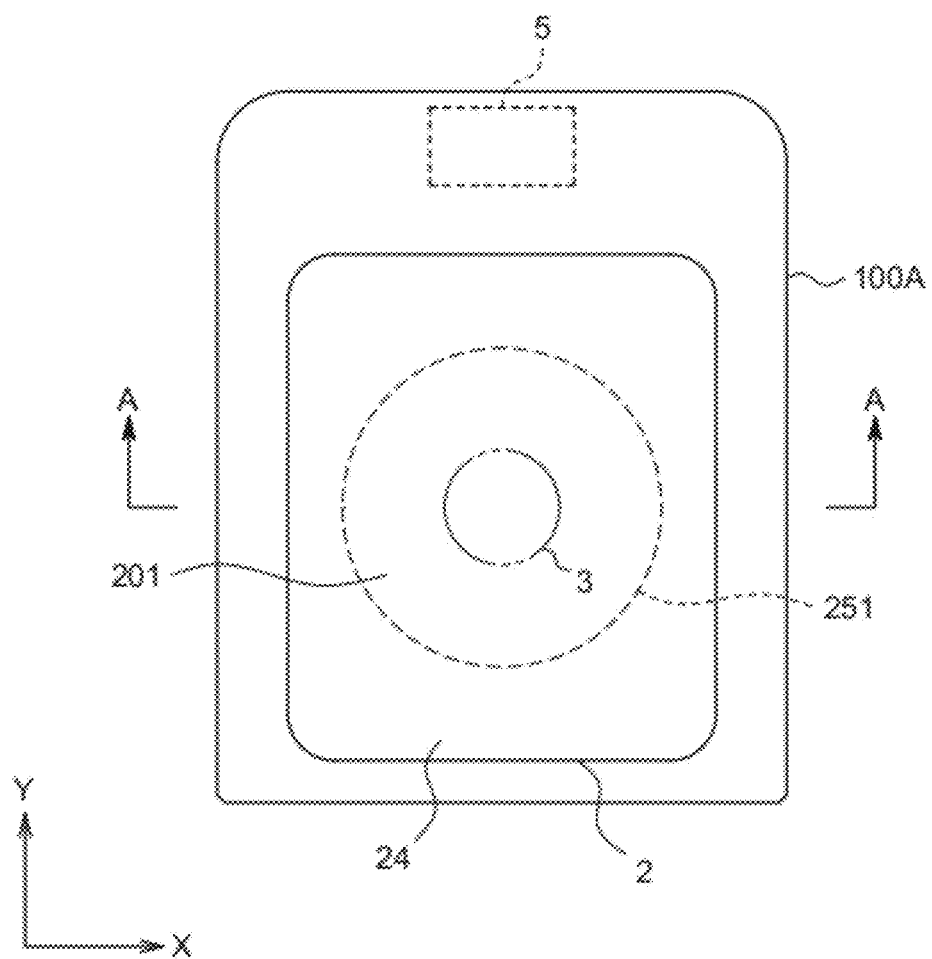
FIG. 6 is a plane view mainly showing a surface luminous part of the intravital observation device of this embodiment.

The surface luminous part 2 is arranged on the device table 100A and irradiates the near-infrared light having a wavelength peak in the region of 800 to 1000 nm onto the living body placing region (X) locating on the upside of the surface luminous part 2. Concretely, the surface luminous part 2 comprises, as shown in FIG. 6 to FIG. 8, an LED loaded substrate 22 whose shape is a general rectangular plate and on which a plurality of LEDs 21 are loaded, a case 23 whose shape is a general rectangle in a plane view and that houses the LED loaded substrate 22 and a light transmissive member 24 that is arranged at an irradiation side of the light from the LEDs 21 in the case 23 and that forms the luminous surface 201.

Figure 7:
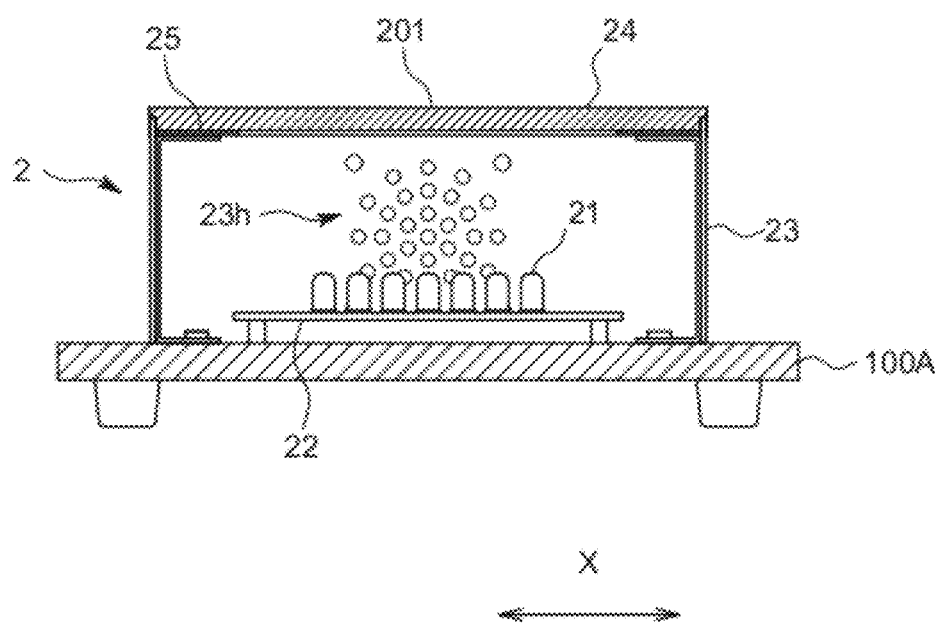
FIG. 7 is a cross-sectional view mainly showing the surface luminous part of the intravital observation device of this embodiment.
Figure 8:
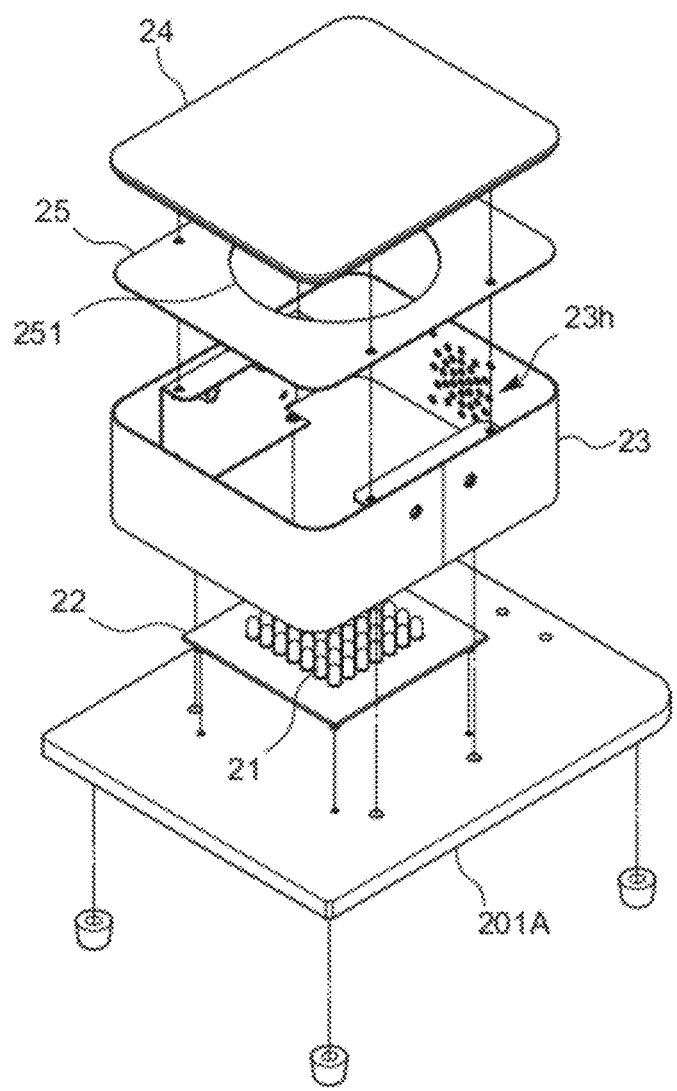
FIG. 8 is an exploded perspective view of the surface luminous part of this embodiment.

The LED loaded substrate 22 is, especially as shown in FIG. 7 and FIG. 8, fixed to a top surface of the device table 100A, and electric power is supplied to the LED loading substrate 2 from an electric power source part 4. In addition, the multiple LEDs 21 are loaded on the top surface of the LED loaded substrate 22, for example, in a state of a matrix. 170 mW of LEDs having a wavelength peak in a region of, for example, 810 nm may be used as the LEDs 21.

The case 23 is, especially as shown in FIG. 7, fixed to the top surface of the device table 100A to surround a circumference of the LED loaded substrate 22, and a plurality of through bores 23h for heat dissipation of the LEDs are formed on one side surface (a back surface located at the back side, in this embodiment). In addition, although not shown in the drawings, a heat dissipation fan for heat dissipation of the LEDs is arranged near the multiple through bores 23h. The electric power is supplied also to the heat dissipation fan from the electric power source part 4.

The light transmissive member 24 is mounted on an upper part opening of the case 23 and is in a shape of a general rectangular plate that is generally the same shape as the upper opening of the case 23 in a plane view. The light transmissive member 24 diffuses the light emitted from the multiple LEDs 21 and makes uniform the luminance of the light irradiated from the upper opening of the case 23 so as to irradiate the even light onto the living body, and is made of, for example, an acetal resin. The top surface of the light transmissive member 24 becomes the luminous surface 201.

In addition, a partition plate 25 that specifies the light from the multiple LEDs 21 in a predetermined range is arranged on a back surface of the light transmissive member 24. The partition plate 25 is in the same shape as that of the light transmissive member 24 in a plane view, and an opening part 251 to irradiate the light from the LEDs 21 to outside (upper part) is formed on a center part of the partition plate 25. With this arrangement, a part corresponding to the opening part 251 of the partition plate 25 on the top surface of the light transmissive member 24 becomes the luminous surface 201. In other words, the luminous surface 201 of the surface luminous part 2 is the same shape as that of the opening part 251 of the partition plate 25 in a plane view.

The imaging part 3 is arranged on the top part of the living body placing region (X), and outputs an image data that indicates the living body perspective image by receiving the light that has passed through the living body placed in the living body placing region (X). For example, a CCD camera or a COMS camera or the like may be used as the imaging part 3.

In addition, the imaging part 3 is fixed to a stand member 5 arranged to stand in a vertical direction to the device table 100A in a state of being able to move back and forth relative to the surface luminous part 2. Concretely, a sliding mechanism 6 is arranged between the imaging part 3 and the stand member 5. The sliding mechanism 6 slidably moves the imaging part 3 relative to the luminous surface 201 in the vertical direction within a predetermined range.

Then, the living body perspective image obtained by the imaging part 3 is output to an information processing unit 7 such as a computer or the like through the electric power supply part 4 (refer to FIG. 4). Then the living body perspective image is displayed on a display part window of the information processing unit 7 and processed by an image processing function of the information processing unit 7. With regard to at least the display part that displays the living body perspective image, the intravital observation device 100 may preliminarily comprise the display part.

Figure 9:
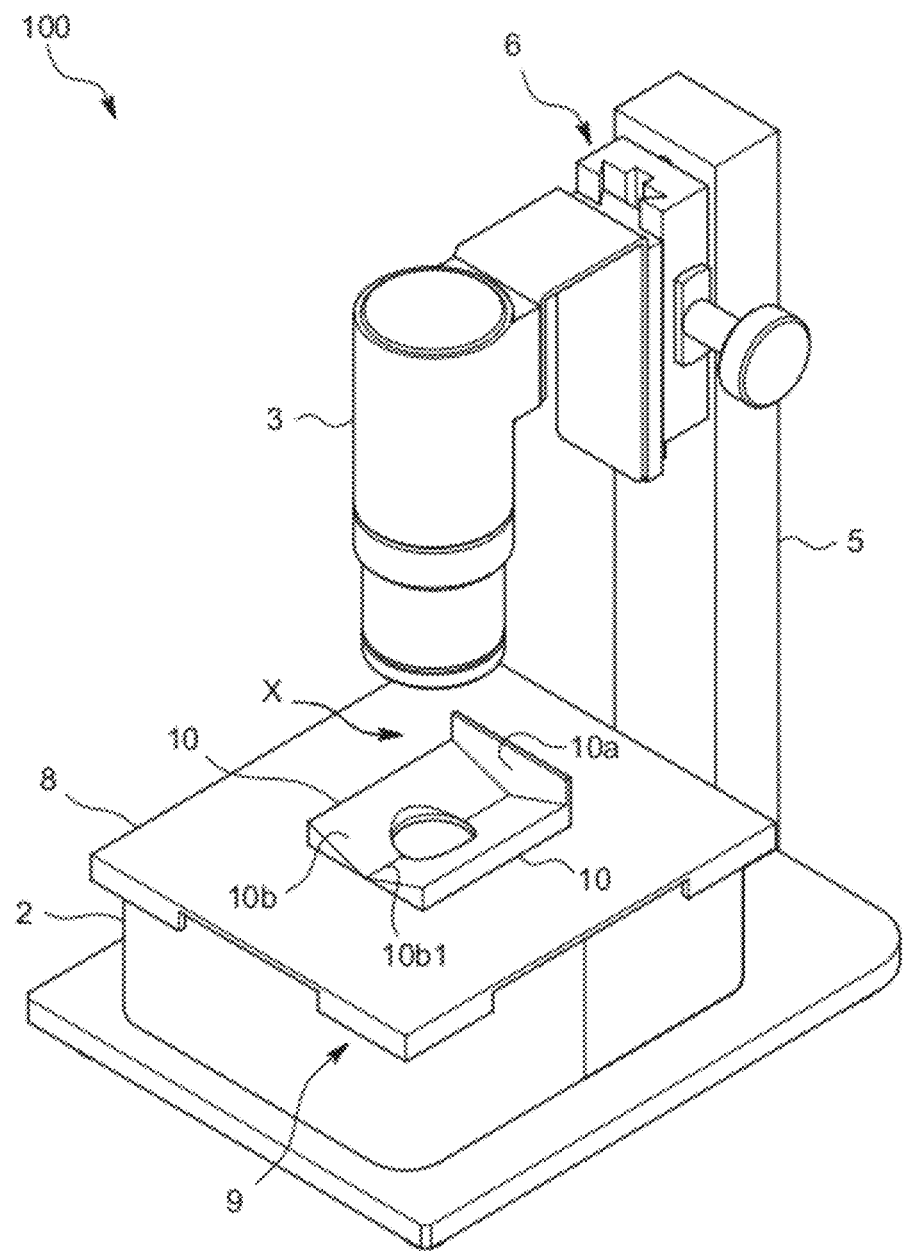
FIG. 9 is a perspective view (with a light shielding member mounted) showing a configuration of the intravital observation device of this embodiment.

The intravital observation device 100 of this embodiment comprises, as shown in FIG. 9 to FIG. 12, a light shielding member 8 that is mounted detachably on the surface luminous part 2 and that blocks a part of the light emitted from the luminous surface 201. FIG. 9 shows a state that the light shielding member 8 is mounted on the intravital observation device 100 in FIG. 5.

Figure 11:
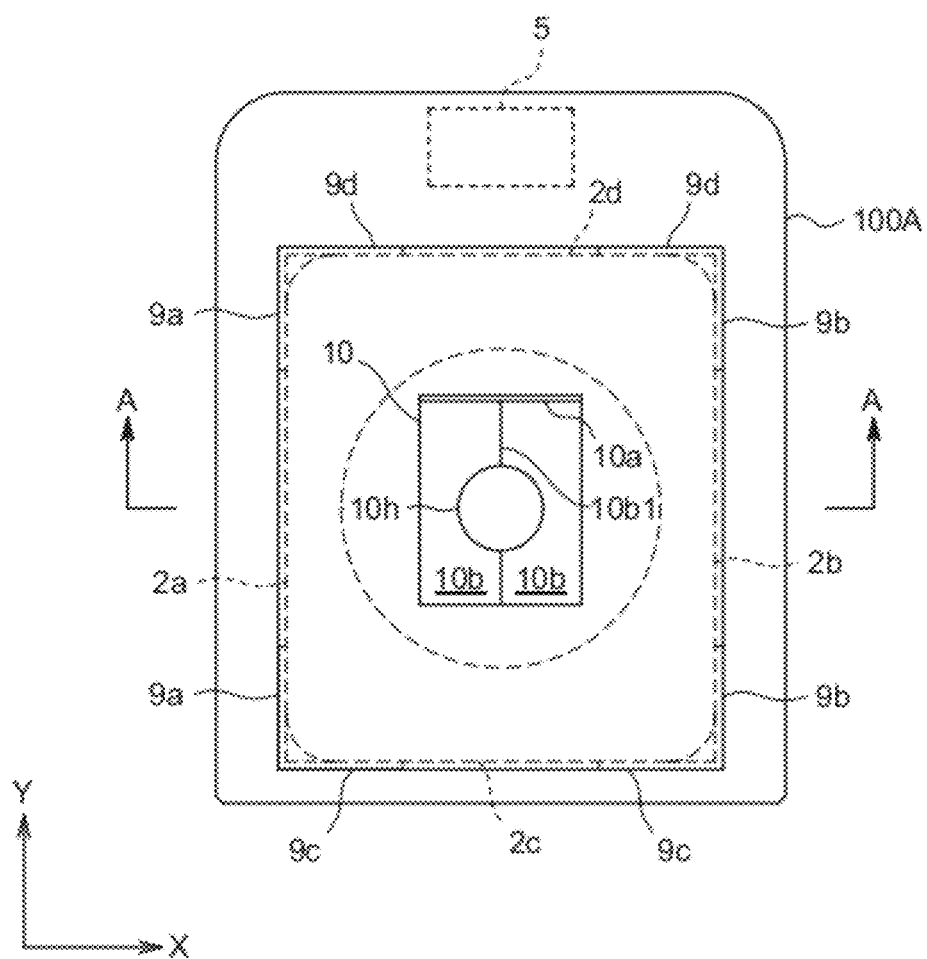
FIG. 11 is a plane view mainly showing the light shielding member of the intravital observation device of this embodiment.

The light shielding member 8 is, especially as shown in FIG. 11, in a shape of a rectangular plate in a plane view that is generally the same as that of the light transmissive member 24 of the surface luminous part 2 in a plane view, and has a light shielding part 81 that blocks the light from the luminous surface 201 and an opening part 82 that passes the light from the luminous surface 201 to the living body placing region (X) side. An opening size of the opening part 82 arranged on the light shielding member 8 is formed to be smaller than the opening part 251 arranged on the partition plate 25. A concrete shape of the opening part 82 is a general circle in a plane view.

Then the light shielding member 8 is mounted on the surface luminous part 2 in a detachable manner by a fixing mechanism 9, to be described later, so as to locate an opening center of the opening part 82 on or near the optical axis 3C of the imaging part 3 (refer to FIG. 10). The opening center of the opening part 82 generally coincides with an opening center of the opening part 251 of the partition plate 25 in a plane view, and the opening center of the opening part 251 of the partition plate 25 is located on the optical axis 3C of the imaging part 3.

The fixing mechanism 9 positions and fixes the light shielding member 8 to the luminous surface 201 of the surface luminous part 2, and concretely the fixing mechanism 9 positions the light shielding member 8 in a direction of a plane of the luminous surface 201. The fixing mechanism 9 of this embodiment is, as shown in FIG. 11, arranged on four side edge parts of the light shielding member 8 and is formed by engaging pieces 9a to 9d that make contact with four side surfaces 2a to 2d of the surface luminous part 2. The engaging pieces 9a to 9d are arranged at four corners of the light shielding member 8. The opening center of the opening part 82 of the light shielding member 8 coincides with the center of the luminous surface 201 of the surface luminous part 2 and the opening center of the opening part 82 of the light shielding member 8 is located on the optical axis 3C of the imaging part 3 by making use of the fixing mechanism 9.

The light shielding member 8 is provided with a positioning member 10 that positions the living body to be tested in a horizontal direction relative to the light shielding member 8 and the luminous surface 201 so as to irradiate the light that is not blocked by the light shielding member 8 on a predetermined portion of the living body.

Figure 10:
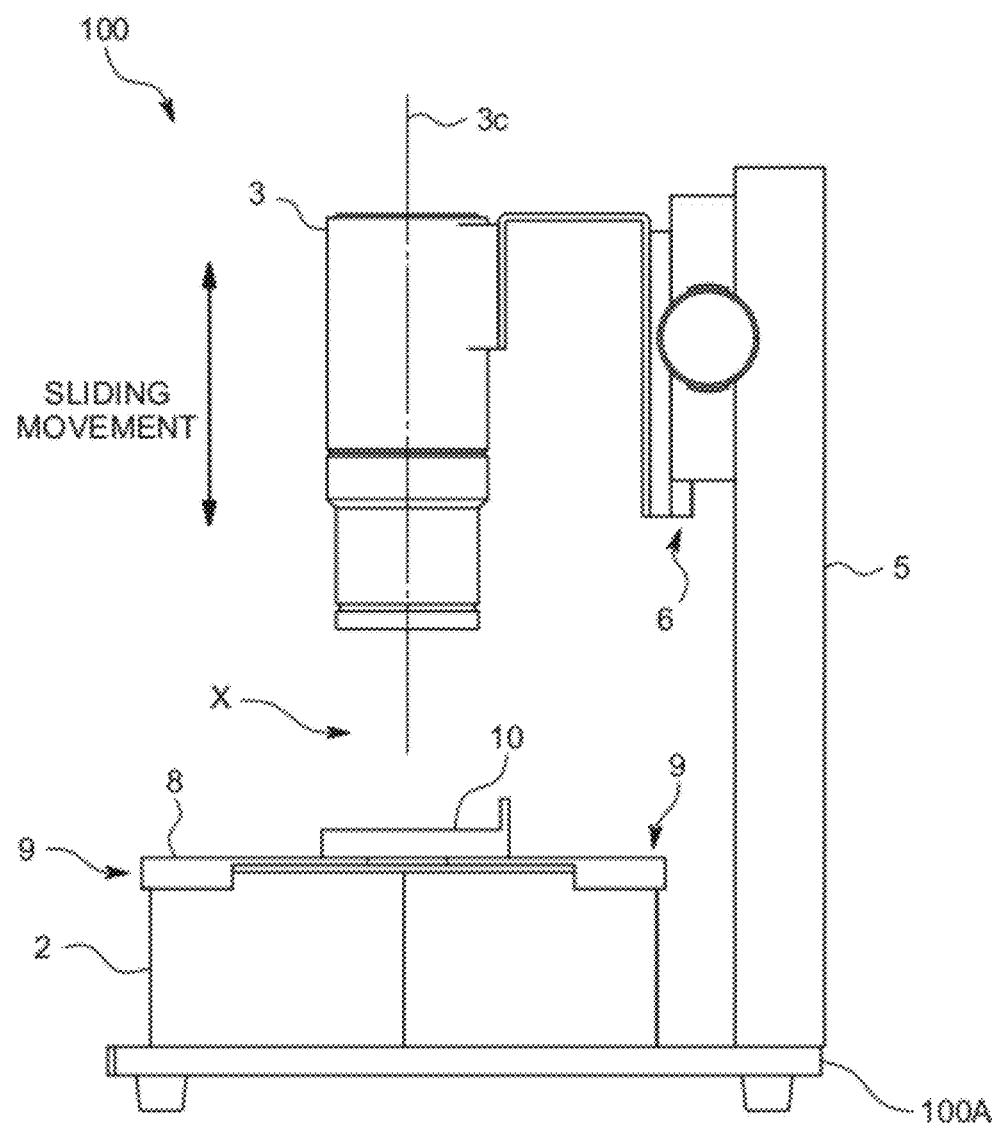
FIG. 10 is a side view (with the light shielding member mounted) showing the configuration of the intravital observation device of this embodiment.
Figure 12:
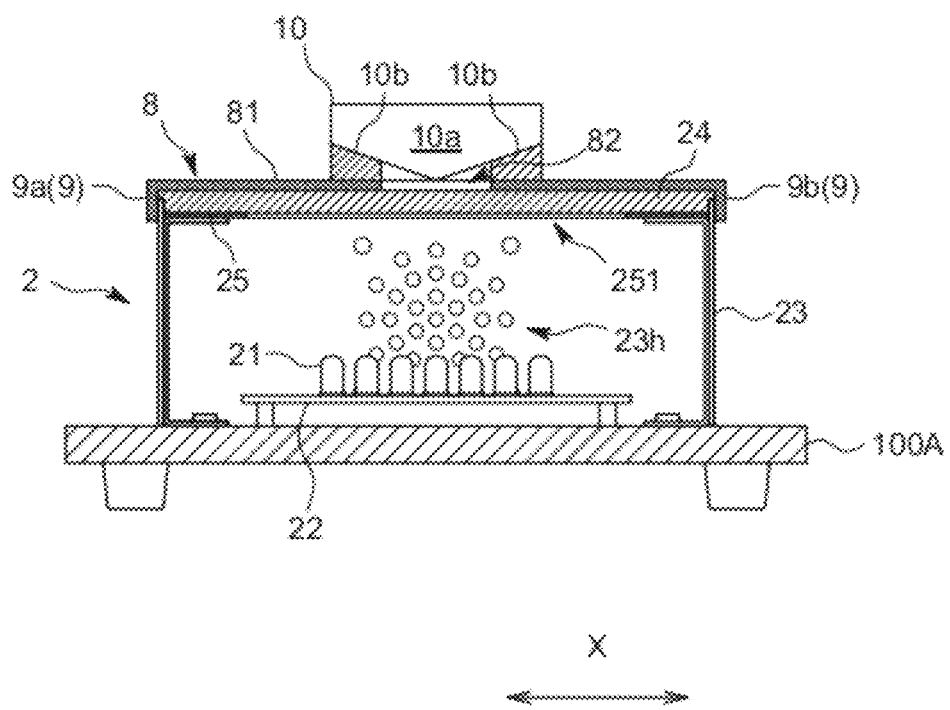
FIG. 12 is a cross-sectional view mainly showing the light shielding member and the surface luminous part of the intravital observation device of this embodiment.

The positioning member 10 of this embodiment makes contact with a predetermined finger and positions the predetermined finger at the opening part 82 of the light shielding member 8, and has, as shown in FIG. 10 and FIG. 12, a through bore 10h that is in communication with the opening part 82 of the light shielding member 8. The positioning member 10 has, as shown in FIG. 9 and FIG. 11, a generally plate shaped first contact surface 10a that is located on the back side (a stand member side) of the opening part 82 and that makes contact with a distal end part of the finger and a generally "V" character shaped second contact surface 10b that is located at the right and the left of the opening part 82 and that makes contact with an arbitrary surface of the finger (for example, a top surface of the finger (a back of the finger)). Then it is so arranged that a valley line 10b1 of the second contact surface 10b passes the center of the opening part 82 of the light shielding member 8. The finger is positioned in the depth direction (Y direction in FIG. 11) relative to the opening part 82 by the first contact surface 10a, and the finger is positioned in the right and left direction (X direction in FIG. 11) relative to the opening part 82 by the second contact surface 10b. Since the opening center of the opening part 82 generally coincides with the optical axis 3C of the imaging part 3, the finger is positioned also to the optical axis 3C of the imaging part 3 by the positioning member 10.

The intravital observation device 100 takes an image of a broad region of the living body in a state that the light shielding member 8 is dismounted, namely a perspective image (concretely, a perspective image of the most part of the hand) of the living body located in a whole range of the luminous surface 201 (refer to FIG. 2(*a*)). Meanwhile, the intravital observation device 100 takes an image of a local area of the living body in a state that the light shielding member 8 is mounted, namely a perspective image of the living body located in a range of the opening part 82 of the light shielding member 8 (concretely, a perspective image of a predetermined portion of a finger) (refer to FIG. 2(*c*)).

<Effect of this Embodiment>

In accordance with the intravital observation device 100 of this embodiment, since the light shielding member 8 that blocks a part of the light emitted from the luminous surface 201 is arranged, a range of light irradiation in the living body placing region (X) can be narrowed so that it is possible to irradiate the light on the local area of the living body. In addition, since the light can be irradiated on the local area of the living body, it is possible to preferably obtain the living body perspective image of the local area of the living body.

Furthermore, since the light shielding member 8 is dismountable from the surface luminous part 2, it is possible to easily switch from obtaining the living body perspective image of the whole of the living body to, such as, for example, a whole of a hand to obtain the living perspective image of a local area of the living body such as a finger just by mounting or dismounting the light shielding member 8. In addition, since the living body is positioned relative to the luminous surface 201 by the positioning member 10, it is possible to irradiate the light on the predetermined area of the living body. Furthermore, since the image of the living body is taken by the imaging part 3 that is positioned relative to the surface luminous part 2, it is possible to simplify a process after the image is taken such as comparing the images obtained by the imaging part 3.

In addition, in accordance with the intravital observation device 100 of this embodiment, it is possible for anyone to observe the foreign material or the blood vessel inside the living body easily without requiring special techniques or experience. Since the inside of the living body can be observed without using the X-rays, even though the light is irradiated onto the living body for a long period of time, it is harmless for the human body, and since the light is just irradiated, a person being tested will never suffer pain when blood circulation is checked. In addition, since the intravital observation device 100 can be downsized easily, it is possible to bring the intravital observation device 100 into a surgery room and to conduct various surgeries while observing the inside of the living body in real time.

<Other Modified Embodiment>

Figure 13:
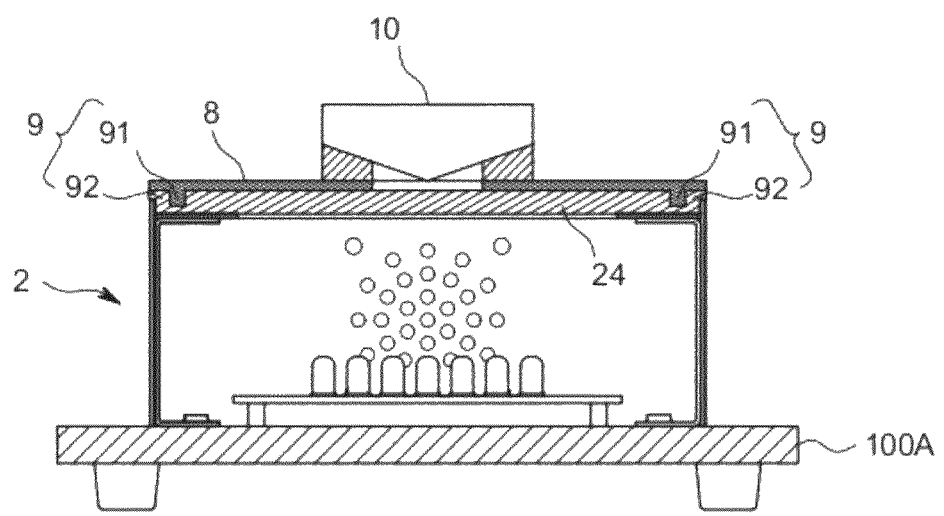
FIG. 13 is a cross-sectional view showing a fixing mechanism of a modified embodiment.

The present claimed invention is not limited to the above-mentioned embodiment. For example, the fixing mechanism 9 may comprise, as shown in FIG. 13, a convex part 91 arranged on the bottom surface of the light shielding member 8 and a concave part 92 arranged on the top surface of the light transmissive member 24. In FIG. 13, a plurality of convex parts 91 and a plurality of concave parts 92 position the light shielding member 8 relative to the light transmissive member 24 in the plane direction, however, the light shielding member 8 may be positioned relative to the surface luminous part 2 in the plane direction by devising a shape of the convex part 91 and the concave part 92. The concave part may be arranged on the bottom surface of the light shielding member and the convex part may be arranged on the top surface of the light transmissive member.

Figure 14:
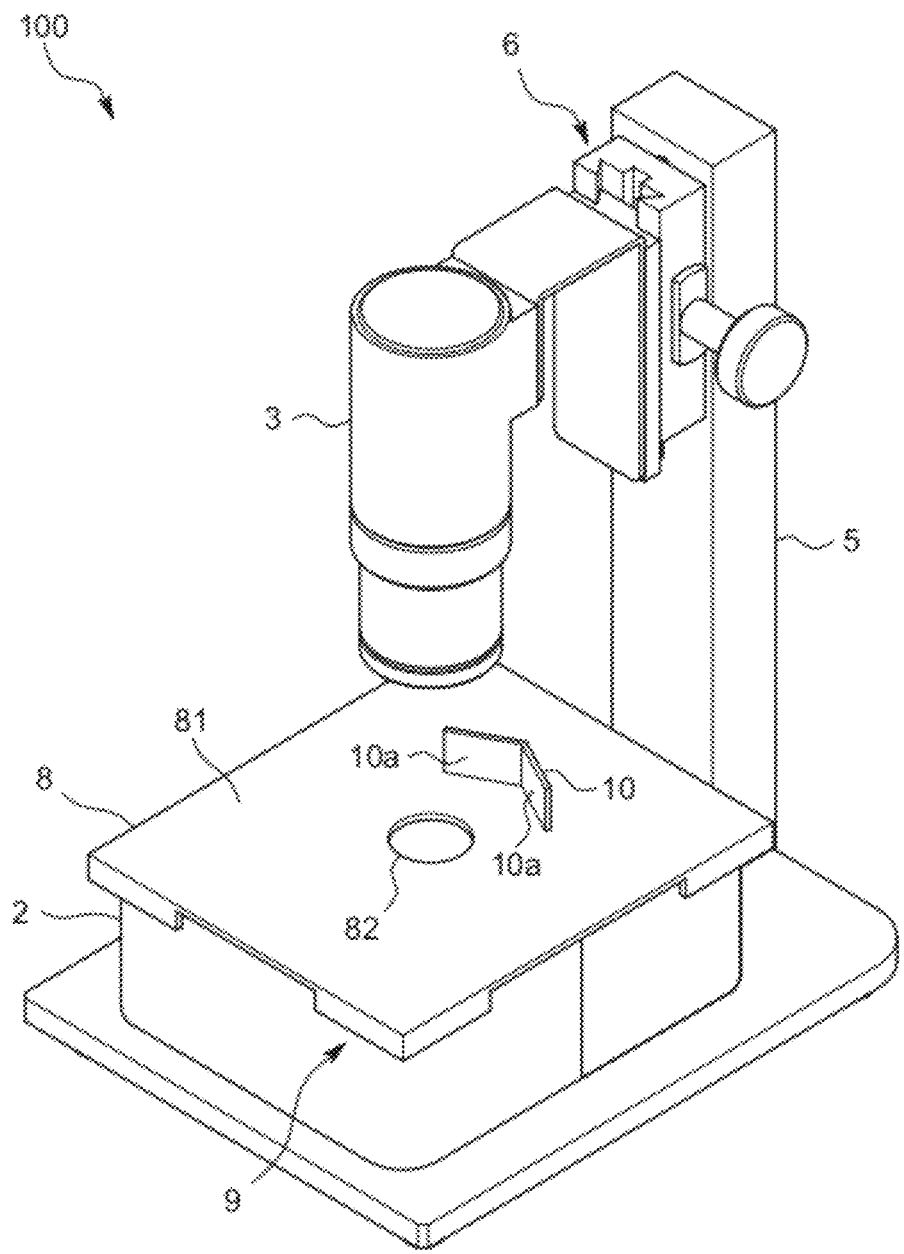
FIG. 14 is a perspective view showing a positioning member in accordance with a modified embodiment.

In addition, the positioning member 10 of this embodiment has the first contact surface 10*a* and the second contact surface 10*b*, however, the positioning member 10 may have only the first contact surface 10*a* or the second contact surface 10*b*. In this case, the shape of the first contact surface 10*a* may be a "V" character shape in a plane view, as shown in FIG. 14, in addition to the plane shape. In this case, it can be conceived that a folded line of the first contact surface 10*a* coincides with a center in the X direction of the opening part 82. Furthermore, with regard to positioning, a positioning line or a positioning figure may be drawn on the top surface of the light shielding member 8. Then it may be so arranged to position the finger relative to the opening part by placing the finger according to the positioning line or the positioning figure.

In addition, the opening part 82 of the light shielding member 8 of the above-mentioned embodiment is generally of a circular shape in a plane view, however, various shapes such as a polygonal shape like a rectangle in a plane view, an elliptic shape, an oblong shape and a partial circular shape in a plane view may be acceptable as far as it can reduce the luminous area of the luminous surface. In this case, it is conceivable that light shielding members having various opening parts tailored to a size of the local area to obtain the living body perspective image may be prepared and the light shielding member is exchanged appropriately in accordance with the usage.

Furthermore, the positioning member of the above-mentioned embodiment is arranged on the light shielding member, however, it may be arranged separately from the light shielding member.

In addition, the positioning member 10 of the above-mentioned embodiment positions the local area (the predetermined area of the finger) of the living body relative to the opening part 82 of the light shielding member 8, however, the living body may be positioned relative to the luminous surface 201 of the surface luminous part 2 on which the light shielding member 8 is not mounted.

The present claimed invention is not limited to the above-mentioned embodiments, a part or all of the above-mentioned embodiment may be appropriately combined without departing from a spirit of the invention.

POSSIBLE APPLICATIONS IN INDUSTRY

As mentioned, in accordance with this invention, it is possible to conduct a surgery of replanting a finger, a hand, an arm, a foot or a leg, a surgery of removing a foreign material or insertion of a catheter while monitoring the inside of the living body in real time. In addition, it is possible to put this invention to practical use in diagnosing a hematogenous disorder or determining vascular constriction due to a chemical drug.

EXPLANATION OF REFERENCE CHARACTERS

1 . . . intravital observation device
2 . . . light source
3, 51 . . . light condensing lens
4 . . . cut filter
5 . . . imaging device
B . . . living body
M . . . display device

The invention claimed is:

1. An intravital observation device comprising:
a light source that irradiates a light having a wavelength peak in a wavelength region of 800 to 1000 nm on a living body, and an imaging device that outputs an image data obtained by receiving the light emitted from the light source having passed through the living body, a surface luminous part that has a luminous surface facing a living body placing region and that irradiates a light onto the living body located in the living body placing region, and a light shielding member that is mounted on the surface luminous part in a detachable manner and that blocks a part of the light emitted from the surface luminous part, wherein the imaging device is a digital camera whose minimum detection light amount per output at a time when receiving light of 0.4 to 10 µW is less than or equal to 0.055 µW/bit, and the imaging device is arranged on a side opposite to the surface luminous part across the living body placing region.

2. The intravital observation device described in claim 1, wherein the light shielding member comprises a light shielding part that blocks the light from the luminous surface and an opening part that transmits the light from the luminous surface to the living body placing region side, and the light shielding member is mounted on the surface luminous part in a detachable manner so that an opening center of the opening part is located on or near an optical axis of the imaging device.

3. The intravital observation device described in claim 1, and having a fixing mechanism that positions and fixes the light shielding member to the surface luminous part.

4. The intravital observation device described in claim 1, and having a positioning member that is arranged on the light shielding member and that positions the living body relative to the light shielding member so that the light from the surface luminous part that is not blocked by the light shielding member is irradiated on a predetermined portion of the living body.

5. The intravital observation device described in claim 1, wherein the surface luminous part comprises a plurality of LEDs, a case that houses the LEDs and a light transmissive member that is arranged on a light irradiation side of the LEDs in the case and that forms the luminous surface.

6. An intravital observation device comprising:

a light source that irradiates light having a wavelength peak in a wavelength region of 800 to 1000 nm on a living body, an imaging device that outputs an image data obtained by receiving the light from the light source having passed through the living body, a surface luminous part that has a luminous surface facing a living body placing region and that irradiates the light from the surface luminous part onto the living body located in the living body placing region, a positioning member that positions the living body relative to the luminous surface of the surface luminous part, and a light shielding member that is arranged between the living body placing region and the luminous surface of the surface luminous part and that blocks a part of the light emitted from the luminous surface, wherein the imaging device is a digital camera whose minimum detection light amount per output at a time when receiving light of 0.4 to 10 µW is less than or equal to 0.055 µW/bit, the imaging device is positioned relative to the luminous surface of the surface luminous part, and the positioning member is arranged on the light shielding member and positions the living body relative to the light shielding member so that the light that is not blocked by the light shielding member is irradiated on a predetermined portion of the living body.

* * * * *